United States Patent [19]

Girard

[11] Patent Number: 5,527,774
[45] Date of Patent: Jun. 18, 1996

[54] DISLOCATION OF CATARACTOUS LENS BY ENZYMATIC ZONULOLYSIS

[76] Inventor: Louis J. Girard, 1428 Twelve Oaks Tower, Houston, Tex. 77027

[21] Appl. No.: 263,860

[22] Filed: Jun. 22, 1994

Related U.S. Application Data

[63] Continuation-in-part of Ser. No. 89,531, Jul. 12, 1993, abandoned.

[51] Int. Cl.$^6$ .................................................. A61K 37/00
[52] U.S. Cl. .............................. 514/12; 514/2; 514/912
[58] Field of Search ................................ 514/2, 12, 912

[56] References Cited

PUBLICATIONS

Kirby: The Early History of Cataract Surgery, SURGERY OF CATARACT 3–18, 1950.
Barraquer J.: Enzymatic Zonololysis, ACTA OPHTHAL-MOLOGICA 36:803–806, 1958.
Barraquer J.: Enzymatic Zonulolysis in Lens Extraction, ARCH OPHTHALMOL 66:6–11, 1961.
Sood N. N., Ratnaraj A.: Couching for Cataract, Hazards and Management, AM J OPTHALMOL 66:687–693, 1968.
Brandt F., Hennig A., Prasad L. N., Rai N. C., Upadhyay M. P.: Results of operative/couching of the lens (a study from Nepal), KLIN. MBL. AUGENHEILK 85:543–546, 1984.
Belyaev V. S., and Barachlov, V. I.: A Modern Experience with Couching for Catarcat, ANNALS OF OPTHALMOL-OGY 14:742–745, 1982.
Chandler P. A.: Choice of Treatment in Dislocation of the Lens, ARCH OPHTHALMOL 71:765–786, 1964.
Grant W. M.: Chymotrypsin. Toxicology of the Eye, Springfield; Charles C. Thomas 1986; 235–239.
Article by Dr. Girard in Ocular Surgery News, Feb. 2, 1993.

Primary Examiner—Zohreh Fay

[57] ABSTRACT

This invention is for a method of treating cataracts in eyes by couching or dislocating of the cataractous lens. It includes the steps of introducing a zonulolysis-causing substance into the interior of the eye adjacent to the cataractous lens in sufficient quantity and strength to produce zonulolysis of the lens zonules normally holding the lens of the eye in place. The zonulolysis-causing substance is maintained in said eye adjacent the zonules until zonulolysis occurs and said lens moves into the inferior cavity of the eye. Alphachymotrypsin is one form of zonulolysis-causing substance. That substance may be introduced through a clear portion of the cornea into the anterior chamber of the eye without rupturing the lens capsule. A quantity of aqueous may be removed from the anterior chamber before introducing the zonulolysis-causing substance. That substance may also be introduced by injection of the substance through the pars plana into the vitreous behind the cataractous lens or by topical application in the presence of means to transport the substance to the lens zonules.

12 Claims, No Drawings

5,527,774

DISLOCATION OF CATARACTOUS LENS BY ENZYMATIC ZONULOLYSIS

This application is a continuation-in-part of my application entitled Method for Treating Cataracts in Eyes by Couching of the Cataractous Lens, numbered Ser. No. 08/089,531 filed Jul. 12, 1993, now abandoned.

BACKGROUND OF THE INVENTION

A. Field of the Invention

This invention relates to a simple and inexpensive method for treating cataractous eyes by couching of the cataractous lens.

B. Background of the Invention

According to the Helen Keller Foundation, there are 28,000,000 people blind from cataract in the world and 17,000,000 blind from cataract in the third world. The numbers double every 20 to 25 years. For example, in India there are approximately 1,000,000 operations for cataract performed every year. Unfortunately, there are 1,500,000 new cataract candidates each year. In spite of the increased efforts of local ophthalmologists and various international organizations, the numbers continue to grow. Not only are there insufficient ophthalmic surgeons but also a lack of equipment. Most efforts entail intracapsular or extracapsular surgery with or without intraocular lens implants.

While intracapsular cataract extraction can be performed without the use of a surgical microscope, this instrument and careful follow-up are necessary for extracapsular surgery, particularly with an intraocular lens. There is also the problem of secondary opacification of the posterior capsule which usually requires the use of a Yag laser, another expensive piece of equipment, or surgical decision. These are all obstacles to a rapid restoration of sight for the majority of people blind from cataracts in the third world.

Couching, the original operation for cataract, performed first by the Hindu, Susruta, Circa 600 B.C., and later adopted by the Greeks, Egyptians and Romans, continued to be the operation of choice right into the 1750's. In couching, the instrument for couching was a curved, "barley-tipped" needle. This was a curved needle, the tip of which was shaped like a barley corn, tapering to a point and was made of brass. The needle was either inserted at the limbus into the anterior chamber and the lens pushed back into the vitreous or it was inserted through the pars plana and the lens dislocated inferiorly. If the lens was completely dislocated without rupturing the lens capsule, the lens would lie in the vitreous cavity in the inferior pole of the eye and the patients would see. Later, when spectacles were available their vision could be restored completely.

Unfortunately, couching often produced a rupture of the lens capsule and the patients would develop uveitis, glaucoma and other complications and 40%–50% would lose their sight.

In spite of the many complications that can occur with couching as a result of the rupture of the lens capsules, the practice continues on in various parts of the world, particularly in India and Nepal. Non-medical healers (couchers) go from village to village in the rural areas performing the technique. Although this practice is condemned by ophthalmologists, some reports are amazingly good. For example, Brandt, Hennig, Prasad, et al. (1984) examined 100 eyes which has undergone couching by "quacks", 1–10 years earlier. At the time of the examination, 42 eyes were found to be blind, most of which occurred immediately after the operation or within six months. The important point was that 68% of the eyes had vision preserved for the first year and subsequent loss of vision was less than 10% per year.

Belyaev and Barachkov two opthalmic surgeons, (1982) reported on 68 eyes which they couched and followed for 5½ years. Vision of 20/20–20/40 was obtained 56/68 (82.4%). In 26 eyes without other pathology vision was 20/20. Eyes with other pathology such as corneal opacification, glaucoma, etc. had a mean visual acuity of 20/50. Mean for both groups was 20/30. There were three complications: one ruptured capsule requiring extraction and two vitreous prolapses into the anterior chamber producing glaucoma which required a vitrectomy.

C. Summary of the Invention

This invention involves the use of an enzyme to perform couching or dislocation of the cataractous lens. The procedure could be performed by a nurse or an ophthalmic assistant in a matter of minutes without the need of a surgical microscope or surgical instruments or prolonged post-operative care.

This invention is for a method of treating of cataracts in eyes by couching or dislocation of the cataractous lens. It includes the steps of introducing a zonulolysis-causing substance into the interior of the eye adjacent the cataractous lens in sufficient quantity and strength to produce zonulolysis of the lens zonules normally holding the lens of the eye in place. The zonulolysis-causing substance is maintained adjacent the lens zonules until zonulolysis occurs and said lens moves into the inferior cavity of the eye. Alphachymotrypsin is one form of zonulolysis-causing substance. That substance may be introduced through a clear portion of the cornea into the anterior chamber of the eye without rupturing the lens capsule. A quantity of aqueous may be removed from the anterior chamber before introducing the zonulolysis-causing substance therein. The substance may also be introduced by injection through the pars plana to a location behind the lens adjacent the lens zonules or by topical application of the substance in a carrier or together with iontophoresis which will cause the substance to move to the interior of the eye adjacent the lens zonules.

D. Description of the Preferred Embodiment

In my invention, couching or dislocation of the cataractous lens is performed by zonulolysis with the use of an enzyme such as alphachymotrypsin. This ensures that the lens capsule remains intact.

One form of the steps of this invention will now be described: The pupil is dilated pre-operatively. The eye is prepared with a topical anesthetic (tetracaine) and disinfectant (povidone iodide 5%). In one form of the invention, the zonulolysis-causing substance is introduced in the following manner: A 30-gauge needle is used to make a beveled incision just inside the limbus into the anterior chamber and approximately 0.25 ml of aqueous removed, but without rupturing the lens capsule. The needle is withdrawn and a second syringe containing alphachymotrypsin 1:5000 is used to inject 0.2 cc into the anterior chamber, again without rupturing the lens capsule. The lens is allowed to dislocate into the inferior vitreous cavity of the eye. In 20 eyebank eyes and in the blind eye of a volunteer, total dislocation took an average of 1.5 hours. There were no complications or pressure rise from the procedure in the eye of the volunteer. A topical antibiotic-steroid ointment can be used to prevent infection and inflammation. The patient is given a pair of spectacles (+12.00 diopter lenses with a +3.00 add). If the treated eye has an intact retina, vision is restored quickly.

When the entire lens, including its intact capsule, is dislocated into the vitreous cavity, it is tolerated very well and will not cause inflammation or glaucoma. These complications only occur when the lens capsule is ruptured and the lens contents are liberated into the eye. Ophthalmologists have observed subluxated (ectopic) lenses tolerated by the eye without inflammation for a lifetime.

A dislocated total lens sinks into the inferior quadrant of the vitreous cavity and causes the patient no symptoms. Sometimes the lens will float into the visual axis if the patient either lies on his back, looking at the ceiling, or puts his head forward, looking at the floor. This is no problem once it is explained to the patient what the phenomenon is.

Patients who are aphakic from a dislocated lens can be corrected to normal vision as long as their retina and macula are normal.

A more specific description of one form of the procedure is as follows:

1. The pupil is dilated preoperatively.
2. A local anesthetic, such as tetracaine, is applied to the eye.
3. A disinfectant, such as povidone iodide, 5%, is applied to the eye.
4. With the patient and operator seated, the operator holds the lids open, using the thumb for the upper lid and the small finger of the other hand for the lower lid.
5. Under slit lamp or loop magnification, the operator inserts a 30 gauge needle on a 1 cc empty syringe into the anterior chamber through a beveled incision in clear cornea near the limbus. Aqueous, 0.25 ml, is aspirated by the assistant and the needle withdrawn. A second syringe and needle is used to inject alphachymotrypsin 1/5000, 0.25 ml, into the anterior chamber (through the same incision, if possible).
6. Pilocarpine 2% and a steroid-antibiotic ophthalmic ointment will be instilled. No bandage is necessary.
7. The alphachymotrypsin is maintained in said anterior chamber until zonulolysis of the lens zonules occurs.
8. At the discretion of the operator, both eyes can be operated on at the same time.
9. Postoperative examination—Operated eyes are observed daily as long as time permits. Patients are given an opportunity to select either +10.00 or +12.00 spectacle with a +3.00 add.

One other method by which enzymatic zonulolysis can be caused to occur is injection of alphachymotrypsin behind the cataractous lens. Preparation of the eye is the same as with the anterior chamber injection, but no aspiration of aqueous is performed. Instead, 0.25 ml. of approximately 1:2500 alphachymotrypsin is injected through the pars plana with a sharp 30-gauge needle. The injection can be made at any point in the pars plana other than the 9 o'clock and 3 o'clock positions where the large vessels and nerves traverse the eye. The operator holds the eyelids apart with the fingers of the two hands. At the same time the needle is inserted through the pars plana 3 mm. from the limbus for a distance of approximately 6 mm. The needle tip should be behind the lens and adjacent to the zonules supporting the lens. An assistant injects the alphachymotrypsin after which the needle is rapidly withdrawn. The lens usually dislocates the moves into an inferior portion of the vitreous cavity within 2-3 hours.

A transient rise in intraocular pressure after the injection of alphachymotrypsin has been reported and extensively investigated. No treatment has been found necessary. The use of pilocarpene drops three to four times a day may be advisable. There is a remote possibility of phacotoxic glaucoma in hypermature lenses.

Couching by alphachymotrypsin introduction is the quickest and simplest method of restoring vision in patients who are blind from cataract. Since the procedure could be performed by a nurse or ophthalmic assistant in a few minutes without the necessity of expensive equipment such as surgical instruments, the operating microscope, the phacoemulsifier, etc., this method is the logical way to restore vision quickly and inexpensively to the 17,000,000 people blind from cataract in the third world. Couching by simple anterior chamber or behind-the-lens injection of 0.25 ml of alphachymotrypsin or other zonulolytic enzyme by non-M.D.'s and the use of mass produced spectacles could solve the problem. The technique could also be offered to the poor and infirm of the industrialized countries.

It can thus be seen that this invention provides a novel method for restoring vision when blindness is caused by cataractous lenses with reduced potential complications to the patient. It is to be understood that various changes may be made in the procedures and quantities involved without changing the concept of the invention hereof.

For example, other means may be used for introducing the zonulolysis-causing substance into the anterior chamber of the eye, as by making a topical application of a zonulolytic substance in a carrier or by other transportation means through the cornea of the eye in sufficient quantity and strength to cause the substance to penetrate the cornea of the eye and be deposited in the anterior chamber.

What is claimed is:

1. A method for treating cataracts in eyes by couching the cataractous lens, the steps comprising:

introducing a zonulolysis-causing substance into the interior of the eye adjacent the cataractous lens in sufficient quantity and strength to produce zonulolysis of the lens zonules normally holding the lens capsule in place; and maintaining said zonulolysis-causing substance adjacent said lens zonules until zonulolysis occurs, thereby permitting said lens to move into the vitreous cavity of the eye.

2. The invention as claimed in claim 1 wherein the zonulolysis-causing substance is chymotrypsin.

3. The invention as claimed in claim 2 wherein the zonulolysis-causing substance is alphachymotrypsin.

4. A method for treating cataracts in eyes by couching of the cataractous lens, the steps comprising:

introducing a zonulolysis-causing substance into the anterior chamber of the eye in sufficient quantity and strength to produce zonulolysis of the lens zonules normally holding the lens capsule of the eye in place; and maintaining said zonulolysis-causing substance in said anterior chamber until zonulolysis of said lens zonules occurs, thereby permitting said lens to move into the vitreous cavity of the eye.

5. The invention as claimed in claim 4 wherein the zonulolysis causing substance is chymotrypsin.

6. The invention as claimed in claim 5 where the chymotrypsin is alphachymotrypsin.

7. The invention of claim 6 wherein the alphachymotrypsin is introduced into said anterior chamber through the clear portion of the cornea of the eye without rupturing the lens capsule.

8. The invention as claimed in claim 4 wherein a quantity of aqueous is removed from the anterior chamber before introducing said zonulolysis substance.

9. A method for treating cataractous eyes by couching of the cataractous lens by zonulolysis, the steps comprising:

injecting alphachymotrypsin into the anterior chamber of the eye through an incision in the clear cornea near the limbus without rupturing the lens capsule of the eye; and maintaining said alphachymotrypsin in said anterior chamber until zonulolysis of the lens zonules occurs, thereby permitting said lens capsule to move into the vitreous cavity of the eye.

10. The invention as claimed in claim 9 wherein a quantity of aqueous is removed from the anterior chamber before injecting said alphachymotrypsin.

11. A method for treating cataracts in eyes by couching of the cataractous lens, the steps comprising:

dilating the pupil of the eye;

applying a local anesthetic to the eye;

applying a disinfectant to the eye;

holding the eye lids open;

inserting a needle into the eye so that the needle tip is located proximate to the lens zonules;

injecting an effective quantity of chymotrypsin into said eye without rupturing the lens capsule of the eye; and maintaining said chymotrypsin adjacent said lens zonules until zonulolysis of said lens zonules occurs, thereby permitting said lens to move into the inferior vitreous cavity of the eye.

12. The invention as claimed in claim 1 wherein alphachymotrypsin is introduced into the interior of the eye by making a topical application of alphachymotrypsin to the exterior surface of the cornea of the eye in sufficient quantity and strength and in conjunction with means to cause the same to penetrate the cornea of the eye and be deposited in said anterior chamber adjacent the lens zonules.

* * * * *